US009452231B2

United States Patent
Nonnenmacher

(10) Patent No.: US 9,452,231 B2
(45) Date of Patent: Sep. 27, 2016

(54) METHOD AND APPARATUS FOR DISINFECTING A CONTAINER

(71) Applicant: Klaus Nonnenmacher, Tuebingen (DE)

(72) Inventor: Klaus Nonnenmacher, Tuebingen (DE)

( * ) Notice: Subject to any disclaimer, the term of this patent is extended or adjusted under 35 U.S.C. 154(b) by 138 days.

(21) Appl. No.: 13/974,222

(22) Filed: Aug. 23, 2013

(65) Prior Publication Data

US 2014/0065013 A1    Mar. 6, 2014

(30) Foreign Application Priority Data

Aug. 30, 2012    (DE) .................. 10 2012 108 042

(51) Int. Cl.
| | | |
|---|---|---|
| *A61L 2/20* | (2006.01) | |
| *B08B 9/08* | (2006.01) | |
| *A61L 2/14* | (2006.01) | |

(52) U.S. Cl.
CPC .................. *A61L 2/202* (2013.01); *A61L 2/14* (2013.01); *A61L 2202/23* (2013.01); *B08B 9/0804* (2013.01); *B08B 2203/005* (2013.01)

(58) Field of Classification Search
CPC ....................................................... A61L 2/202
USPC ........................................................ 422/24
See application file for complete search history.

(56) References Cited

U.S. PATENT DOCUMENTS

| | | | |
|---|---|---|---|
| 3,383,163 A | | 5/1968 | Menashi |
| 5,733,512 A | * | 3/1998 | Tsai ................... C01B 13/11 422/186.15 |
| 5,928,607 A | * | 7/1999 | Frisk ..................... A61L 2/10 422/24 |
| 2002/0061403 A1 | * | 5/2002 | Liou et al. .............. 428/434 |
| 2004/0140269 A1 | | 7/2004 | Chang |
| 2005/0089458 A1 | * | 4/2005 | Oke ....................... 422/207 |
| 2008/0167650 A1 | * | 7/2008 | Joshi et al. ................ 606/41 |
| 2009/0114605 A1 | * | 5/2009 | Salama et al. ............ 210/748 |
| 2012/0121457 A1 | * | 5/2012 | Farren ........................ 422/3 |
| 2012/0231182 A1 | * | 9/2012 | Stevens ................ A61L 2/14 427/576 |
| 2014/0015171 A1 | | 1/2014 | Herold et al. |

FOREIGN PATENT DOCUMENTS

| | | |
|---|---|---|
| DE | 3502242 A1 | 7/1986 |
| DE | 19542447 A1 | 5/1997 |

* cited by examiner

*Primary Examiner* — Kevin Joyner
*Assistant Examiner* — Holly Mull
(74) *Attorney, Agent, or Firm* — Andrew Wilford

(57) ABSTRACT

An apparatus for disinfecting an interior of a generally closed container having an opening has an elongated housing fittable through the opening, having a wall forming a reaction chamber, and having an inner end and an outer end longitudinally flanking the chamber. Thus when the outer end is tilted to the opening, the inner end is in the interior of the container. An ozone generator is provided in the chamber. A plurality of openings in the wall of the housing at the inner end conduct ozone from the chamber out into the interior of the container.

15 Claims, 7 Drawing Sheets

METHOD AND APPARATUS FOR DISINFECTING A CONTAINER

FIELD OF THE INVENTION

The present invention relates to the disinfection of a container. More particularly this invention concerns a method of an apparatus for disinfecting the interior of a relatively closed container, such as barrel or keg.

BACKGROUND OF THE INVENTION

Disinfecting a container, in particular in the food industry, is generally carried out using fluids and, if necessary, by additional mechanical treatment. In addition, sulfur dioxide ($SO_2$) gas is traditionally used for disinfecting wooden barrels. For this purpose, for example sulfur sticks are burned or carbonized inside the wooden barrel.

In addition to the biocidal effect of sulfur dioxide gas, the biocidal effect of sulfites takes place in aqueous solution that, for example can be obtained through solution equilibriums between the gas phase and (residual) moisture on surfaces, primarily through the undissociated form of sulfuric acid ($H_2SO_3$). In order for the latter to achieve an optimum effect, a low pH value is thus required, preferably below 3. Consequently, this means that the containers used for foodstuff, in particular wooden barrels, have to be freed from degradation products and acidic residues by cleaning with sterile water after the sterilization process. For complete removal and disinfection, this has to be done thoroughly and therefore involves significant expenditure of time.

The biocidal effect of sulfur dioxide and the sulfites is in particular based on their reduction effect. In the process of this, the available oxygen is rapidly absorbed by sulfur dioxide and the sulfites so that the aerobic organisms cannot perform a metabolic process and consequently die off. In contrast, the biocidal effect with respect to anaerobic microorganisms is poor.

Furthermore, using sulfur dioxide for disinfecting wooden barrels results in the wood absorbing the disinfecting sulfur dioxide gas, and residues of sulfur dioxide are still present in the wood, even after extensive cleaning with water. After filling the barrels with foodstuff such as, for example wine, these residues are released into the food stuff, which can result in excessive sulfite contents. In view of the biocidal effect of the sulfites, this poses an undesirable health burden. Uncombined sulfites are known for causing pseudoallergic and anaphylactic reactions after inhalation and oral ingestion. Furthermore, sulfites are a skin and mucosa irritant.

OBJECTS OF THE INVENTION

It is therefore an object of the present invention to provide an improved method and apparatus for disinfecting containers.

Another object is the provision of such an improved method and apparatus for disinfecting containers that overcomes the above-given disadvantages, in particular that allow disinfecting containers and in particular wooden barrels without requiring elaborate cleaning or post-cleaning, and in particular in such a manner that no residues remain in the containers that contaminate the foodstuff and can have a negative effect on the health of consumers of the foodstuff.

Furthermore according to the invention the disinfection effect should be at least as good as the known methods and preferably even better.

SUMMARY OF THE INVENTION

An apparatus for disinfecting an interior of a generally closed container having an opening has according to the invention an elongated housing fittable through the opening, having a wall forming a reaction chamber, and having an inner end and an outer end longitudinally flanking the chamber. Thus when the outer end is tilted to the opening, the inner end is in the interior of the container. An ozone generator is provided in the chamber. A plurality of openings in the wall of the housing at the inner end conduct ozone from the chamber out into the interior of the container.

The phraseology "at" the inner end is mentioned hereinafter, this refers to the portion of the housing that corresponds to that half, preferably to that third of the housing that ends at the inner end.

Using ozone as a disinfectant has the advantage that hereby aerobic and likewise anaerobic microorganisms can be completely killed. Hereby, even at pH values around 7, that is, in the neutral range, kill rates can be achieved that leave no detectable residual germ contents. Ozone penetrates as a gas in every corner of the container, and when used in wooden containers, can even penetrate into the wood and thus can effect an optimal disinfection of the entire container. In addition, the ozone generator of the apparatus makes it possible to provide the ozone within the container. For this purpose, the ozone generator is in the elongated housing. This elongated housing allows inserting the entire apparatus into the container through a normally already existing opening of the container, for example a filling opening or a pour opening, the bunghole of a barrel or keg. In this manner, the end designated here as the inner end is placed in the container and ensures that the ozone generated by the ozone generator can diffuse into the interior of the container through the plurality of openings at the inner end.

For this purpose, the ozone generator is preferably also arranged at the plurality of openings. Thus, the gas already present in the container, normally air, can be used as the carrier gas for the ozone used. This gas diffuses through the plurality of openings to the ozone generator, and the oxygen present in the air can be converted into ozone at this ozone generator. Supplying ozone with an ozone generator outside of the container is therefore not necessary, and therefore there is no hazard to the health of the user of this apparatus according to the invention. Thus, as a result, the container is completely disinfected and, furthermore, undesirable and disturbing odor and flavor carriers are removed by the oxidation with ozone. Due to the compact arrangement with the ozone generator in the housing and the simple insertability into a container to be disinfected through already existing openings, the apparatus according to the invention is simple to use.

In an inventive configuration of the apparatus, the housing has a round cross-section, so that it is cylindrically tubular. This housing shape has the advantage that as a result, the apparatus according to the invention can be inserted in a simple manner into openings that are usually round in the respective containers such as, for example wooden barrels.

In another configuration of the apparatus according to the invention, the housing is made from metal. Using metal, preferably stainless steel, has the advantage that in this manner, a material is used for the housing that, on the one hand, is not susceptible to the disinfectant ozone and therefore is not damaged by it and, at the same time, it is a material that can be cleaned and optionally disinfected in a simple manner.

In another configuration of the apparatus according to the invention, the housing has on the outside of its outer end a sealing element by means of which the apparatus can be sealingly received in an opening of the container, formed basically as a tapered plug.

This configuration ensures that the apparatus can be inserted in a sealing manner into a container such as, for example a wooden barrel. Ozone provision or generation then takes place within the container that, provided that there are no further open openings, represents a chamber that is completely sealed from the external surroundings and in which a preferably continuous ozone generation takes place without allowing the ozone to escape to the outside. This further reduces danger to the users of the apparatus according to the invention and in general to other surroundings. After completion of the disinfection, the ozone generation is stopped, and after a certain waiting time during which the remaining ozone in the container has oxidized back into $O_2$, the apparatus is removed from the opening of the container. Thus, any health hazard to the surroundings is completely excluded.

In another configuration of the apparatus according to the invention, the plurality of openings in the housing is configured as round holes. Configuring the plurality of openings as round holes has the advantage that the holes can be formed in the housing in a comparatively simple manner and, apart from that, already known methods can be used for producing such housings.

In an alternate configuration of the apparatus according to the invention, the plurality of openings in the housing is configured as longitudinal slots. Using longitudinal slots has the advantage that a comparatively large opening can be provided that enables a simple and effective conduction of atmospheric oxygen into the apparatus and of ozone out of the apparatus, for example by diffusion. Apart from that, these openings can also be also provided in such a manner that the structural integrity of the entire elongated housing is not negatively influenced. The longitudinal slots can be arranged with regard to the longitudinal direction of the elongated housing in such a manner in the housing that they extend transverse, parallel or diagonal to the longitudinal or axial direction. Preferably, the slots extend transverse or diagonal to the housings axis and particularly preferred perpendicular thereto.

In a further configuration of the apparatus according to the invention, the ozone generator comprises an induction electrode and a discharge electrode that are separated from one another by a solid dielectric. Such an ozone generator has the advantage that it can provide ozone while being operated with low voltage and low power consumption, for example at 12 V and less than 500 mA. Nevertheless, an effective amount of ozone is provided here that ranges, for example, between 10 and 50 mg $O_3$/h. Furthermore, due to the heat generation on the discharge electrode located on the outside or on the dielectric located between the electrodes, convection and hence air flow is generated. This facilitates in addition the inflow of atmospheric oxygen from outside of the apparatus into the housing of the apparatus and also the transport of generated ozone from the internal chamber of the housing of the apparatus to the outside into the interior of the container, for example into the interior of the wooden barrel.

In an alternate configuration of the apparatus according to the invention, the ozone generator has a first pointed electrode and a second electrode formed by the housing and, viewed in the longitudinal direction, the housing has at least one opening at the level of the pointed electrode. The edge of the opening is spaced from the point of the electrode for arcing or sparking therebetween to generate ozone.

This configuration of the ozone generator has the advantage that an electron spray is generated here that, extending from the pointed electrode, leads toward the edge of the opening in the housing. Due to the kinetic energy of the electrons and also of the potentially created ions and radicals, the latter are accelerated toward the opening edge in the housing and thus can get from the housing into the interior of the container. This way, convection within the housing of the apparatus is enhanced and, at the same time, is directed away from the pointed electrode. The result of this is, among other things, that the formation of condensates that can develop in the discharge region, the so-called plasma, of other ozone generators, is avoided.

In another configuration of the apparatus according to the invention, the apparatus further comprises a UV light source that is arranged in the housing. Using a UV light source has the effect that from the generated ozone, together with, for example water (vapor) present in the interior of the container, peroxides, in particular hydrogen peroxide, can be formed under the influence of the UV radiation from the UV light source. On the one hand, they themselves contribute to the disinfection of the container and, furthermore, they can serve as a base substance or starting substance for radical chain reactions. These radical chain reactions, in turn, are initiated by the UV radiation emitted from the UV light source and, if necessary, are also maintained. When viewed in the longitudinal direction, the housing of the apparatus preferably has no openings at the level of the UV light source so that the UV light cannot exit here directly from the internal chamber of the housing, but is first reflected on the inner housing wall and thus is enhanced. Apart from these effects, the UV light source is also a heat source that, in addition, enhances the already mentioned convection of the atmospheric oxygen into the housing and of the formed ozone out of the housing. Furthermore, in preferred configurations, the housing can be configured such that taking up water is possible in the inner end of the housing, which water evaporates due to the convection and/or the heat and thus facilitates the already explained peroxide formation.

In a further configuration of the apparatus according to the invention, the apparatus further comprises a UV light source that is arranged on the outside of the housing. Providing a UV light source outside the housing, preferably at the inner end, ensures that first ozone can be formed within the housing without being converted immediately together with water into hydrogen peroxide under the influence of UV radiation. Due to the external arrangement of the of UV light source, this reaction occurs only after the ozone has passed, through diffusion and the already mentioned convection, from the internal chamber of the housing to the outside and into the interior of the container.

In a preferred configuration of the apparatus, the bottom of the apparatus, thus in particular the housing at the inner end, consists at least partially of an inert material, for example stainless steel, plastic, aluminum, silver, palladium or the like. Combinations of these materials can also be used. Hereby, stability and service life of the apparatus can be further improved and extended. Moreover, an inert material makes it easier to clean and disinfect the apparatus.

Furthermore, at the inner end, the housing can comprise, at least partially, a metal oxide, in particular an oxide layer or coating. This way, catalytic effects are achieved during the conversion of ozone to enhance the effectiveness of the apparatus according to the invention. Particularly suitable is, for example, a coating or an oxide coat from aluminum oxide and/or copper oxide and/or manganese oxide. The coating can be, for example, on or at the lower end of the housing, in particular at the bottom cap or the bottom cover. The oxide coating or the coat can be applied on the inside and/or outside. The surface area of the bottom cover is generally sufficient for achieving a very effective support for the effectiveness of the apparatus through the catalytic effect of the oxide material. In addition, in particular the bottom cover is well suited for providing the oxide material thereon since then the remaining housing can be provided with an inert surface, for example, stainless steel.

Furthermore, the above-described object is achieved by a method for disinfecting the interior of wooden containers by providing ozone in the wooden container. According to the above explanations, disinfecting the wooden containers, in particular wine barrels, with ozone has the advantage that the previously used disinfection by sulfur dioxide can be dispensed with. Thereby, the already discussed health hazard through foodstuff that can be affected by the increased sulfite content is reduced. Furthermore, the disinfection effect of the ozone is also given in the case of anaerobic microorganisms so that even the disinfection as such with ozone as the disinfectant is improved with respect to sulfur-dioxide disinfection.

In a further configuration of the method according to the invention, the ozone is generated in a wooden container. By generating ozone directly in a wooden container, external generation of ozone including further supply lines into the container is not required. This reduces the risk of ozone escaping on the way into the wooden container. As a result, hazard to the user of the method according to the invention caused by ozone or ozone leaks is significantly reduced.

In a further configuration of the method according to the invention, the method comprises the following steps:
  providing an ozone generator in the wooden container,
  closing the container, and
  generating ozone by the ozone generator.

Through these method steps according to the invention, the advantageous generation of ozone in the wooden container as already mentioned above is implemented. For this purpose, the wooden container is also sealed after an ozone generator is inserted into the wooden container. In this manner, not only a hazard to the users of the method according to the invention caused by ozone leaks in the supply lines is eliminated, but a hazard caused by ozone escaping from the wooden container is also avoided. Thus, the ozone is generated in a sealed atmosphere within the wooden container, as a result of which disinfection takes place over a defined period within the wooden container and therefore also on the inner walls thereof.

In a further configuration of the method according to the invention, generating ozone is carried out continuously. Continuously generating ozone has the advantage that in this manner, an ozone-containing atmosphere can also be maintained in the wooden container over a predetermined period with possibly low amounts of generated ozone. The result of this is that, accordingly, microorganisms present in the wooden container are killed bit by bit within this period. After finishing the ozone generation, the wooden container preferably still remains closed for some time until the still remaining ozone in the wooden container is degraded. Disinfection using ozone is therefore residue-free and potential subsequent health problems caused by the disinfectant are excluded.

In another configuration of the method according to the invention, furthermore, the interior of the wooden container is exposed to UV light. Exposing the interior to UV light has the advantage that in this manner, hydrogen peroxide can be formed from the ozone together with water still present in the atmosphere of the interior of the wooden container. The hydrogen peroxide likewise reacts as disinfectant to the microorganisms present in the wooden container. Also, hydrogen peroxide has the advantage that it is degraded without residues and therefore no further health burden is caused by this disinfectant. Furthermore, UV light can be used for faster degradation of the remaining ozone after the ozone generation.

In another configuration of the method according to the invention, furthermore, water vapor is provided in the interior. By providing additional water vapor, the above-mentioned formation of hydrogen peroxide is also assisted by the UV light. Generating the water vapor can be carried out by a separate water evaporator in the interior of the wooden container, or can also be performed by the same apparatus that also provides the ozone.

By providing a metal oxide at the bottom of the apparatus that can be used for the method, thus, at the inner end of the housing, advantageously, catalytic effects are achieved during the conversion of the ozone that enhance the effectiveness of the method according to the invention. Particularly suitable is an oxide coating or an oxide coat, for example from aluminum oxide and/or copper oxide and/or manganese oxide. Furthermore, the housing itself can at least partially consist of an inert material, for example stainless steel, plastic, aluminum, silver, palladium or the like. This way, stability and service life and also handling of the apparatus can be further improved and extended.

It is to be understood that the features mentioned above and yet to be explained hereinafter can be used not only in the respectively specified combination, but also in other combinations or alone, without departing from the scope of the present invention.

BRIEF DESCRIPTION OF THE DRAWING

The above and other objects, features, and advantages will become more readily apparent from the following description, it being understood that any feature described with reference to one embodiment of the invention can be used where possible with any other embodiment and that reference numerals or letters not specifically mentioned with reference to one figure but identical to those of another refer to structure that is functionally if not structurally identical. In the accompanying drawing.

DETAILED DESCRIPTION OF THE INVENTION

As seen in FIGS. 1 to 9 the apparatus of this invention is shown in five different embodiments at 10, 12, 14, 16 and 18. Identical features between the respective embodiments are in each case designated by identical reference numbers.

Figure 1:
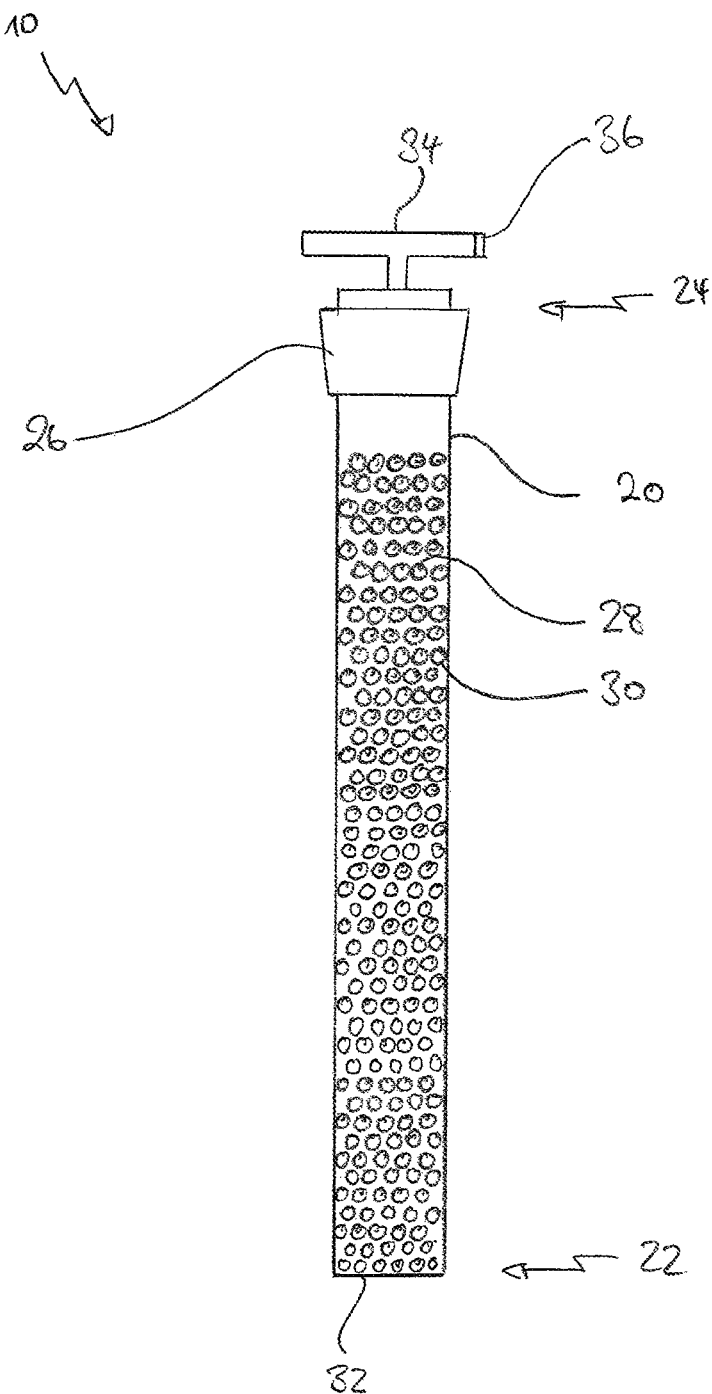
FIG. 1 is a side view of a first embodiment of an apparatus according to the invention.

The apparatus 10 in FIG. 1 has an elongated cylindrically tubular housing 20 centered on a vertical axis with an lower inner and an upper/outer 24 opposite the inner end 22. The apparatus 10 forms a chamber inside the housing 20, in which an unillustrated ozone generator is arranged. The ozone generator is not shown here in detail in FIG. 1 and within the context of the apparatus 10, but is described and in more detail hereinafter in connection with the embodiment of the apparatus 12 and the FIGS. 2-7.

the outer end 24 of the tubular housing 20 is closed by a sealing element 26. In the present embodiment, this sealing element 26 is formed like a plug with a frustoconical outer surface, tapering from the outer end 24 toward the inner end 22. The sealing element 26 can preferably be made from an elastic material, preferably a rubber-like material that is selected such that it is not or only insignificantly susceptible to ozone. Non-limiting examples for such rubber-like substances are, for example synthetic rubber such as, for example ethylene-propylene-dien-monomer or type M rubber (EPDM), and particularly preferred silicones or silicone rubbers. Alternately, inelastic sealing elements can also be used, which preferably also consist of ozone-resistant substances. Examples for this can be sealing elements made from stainless steel or preferably polytetrafluoroethylene (Teflon®).

Viewed from the outer end 24 toward the inner end 22, a multiplicity of openings 28 are arranged inward of the sealing element 26 in the housing 20 of the apparatus 10. In the present case, these openings 28 are round holes 30. Here, the openings 28 and/or round holes 30 extend the full length of the housing 20, down to the inner end 22 and also circumferentially all around the housing 20.

Apart from that, the inner end 22, of the cylindrically tubular housing 20 is closed with a flat cover disk 32 that either be solid for formed like the side wall of the housing 20 with the holes 30.

At its outer end 24, the housing has a handle 34 that, on the one hand, serves for holding the apparatus 10 with the hand when inserting the apparatus 10 according to the invention into or removing it from a container to be disinfected. Furthermore, the handle 34 also has a power connector 36 through which electrical power can be supplied to the unillustrated the ozone generator in the housing 20. For this, a live cable is plugged into this power connector 36. For this purpose, the power connector has well-established connecting formations such as for example sockets.

Figure 2:
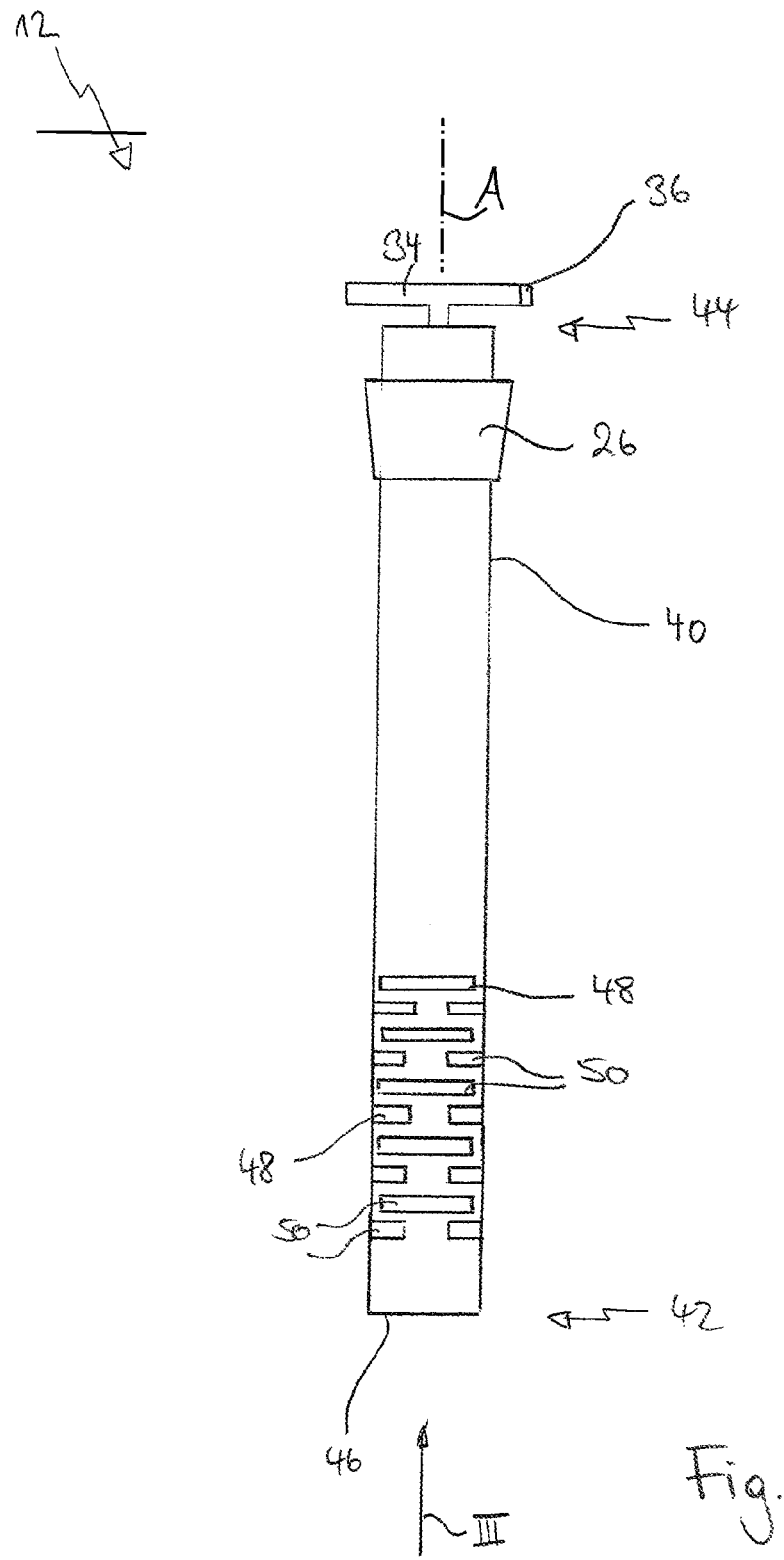
FIG. 2 is a side view of a second embodiment of an apparatus according to the invention.
Figure 3:
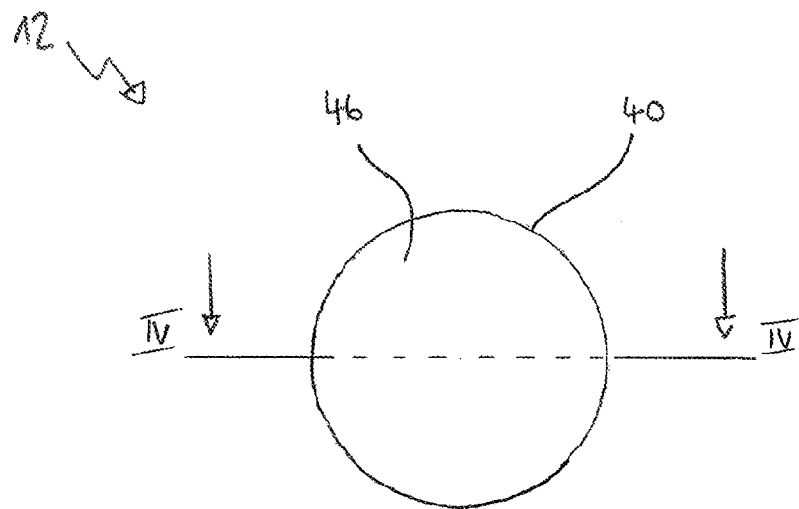
FIG. 3 is an end view taken in the direction of arrow III of FIG. 2.
Figure 4:
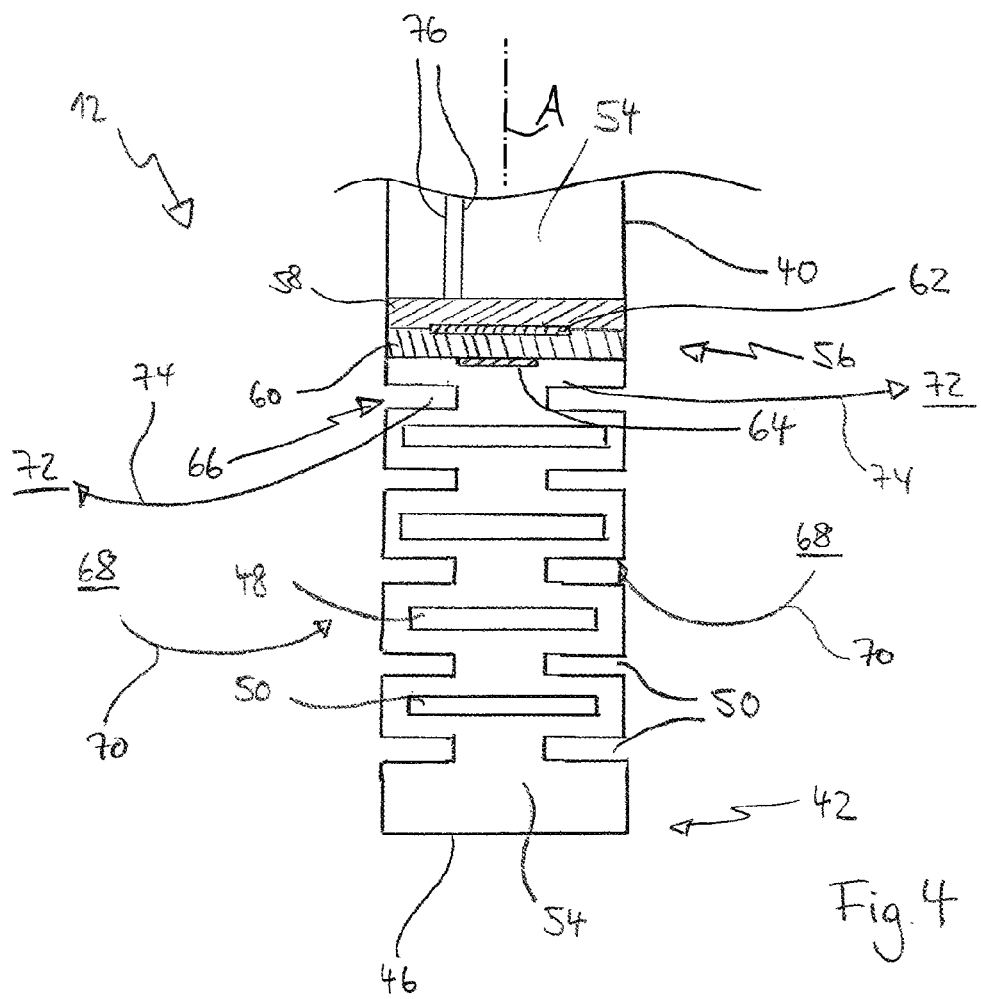
FIG. 4 is a large-scale section taken along line IV-IV of FIG. 3 of the inner end of the apparatus of this invention.

The second embodiment of the apparatus 12 in FIGS. 2-4 likewise has a housing 40 having an inner end 42 and an outer end 44. This housing 40 of the apparatus 12 is also tubularly cylindrical, that is elongated and with a circular cross-sectional shape as clearly visible in FIG. 3. FIG. 3 shows here that the inner end 42 of the housing 40 is closed by a cover disk 46.

The apparatus 12, like the apparatus 10, has at the outer end 44 a handle 34 with a power connector 36. Furthermore, at the outer end 44, there is a sealing element 26.

While the openings 28, thus the round holes 30, extend in the embodiment of the apparatus 10 from FIG. 1 over almost the entire length of the housing 20, the apparatus 12 has openings 48 that are only adjacent the inner end 42. Provision of them at the inner end 42 means here that the openings are here only in the inner half, preferably in the last third, of the overall axial length between the outer end 44 and the inner end 42, and therefore toward the inner end 42 in the housing 40.

The openings 48 in the apparatus 12 are configured here as elongated slots 50 each lying in a respective plane perpendicular to the axis A (FIG. 4) of the housing 40. In accordance with the above explanations in connection with the apparatus 10 in FIG. 1, here too, the slots 50 extend angularly around the housing 40 and therefore through an angle of around 90°, with two slots 50 diametrally opposite each other and the next two slots 50 offset angularly to them by 90°.

FIG. 4 is a section through the apparatus 12 at the inner end 42. The apparatus 12 and/or the housing 40 has an internal chamber 54 holding an ozone generator 56. In this specific embodiment of the apparatus 12, the ozone generator 56 is at that end of the array of openings 48 toward the outer end 44. With regard to the illustration of the FIGS. 2 and 4, the ozone generator 56 is therefore located above or outward of the openings 48.

In this embodiment, the ozone generator 56 has two ceramic halves 58 and 60. Between these ceramic halves 58 and 60 is an induction electrode 62. On the lower or outer side of the ceramic half 60 and, in the example shown here, toward the openings 50, a discharge electrode 64 is arranged on the ceramic half 60. Thus, the induction electrode 62 and the discharge electrode 64 are separated by a dielectric, in this embodiment by the ceramic half 60. For insulation purposes, the outer discharge electrode 64 can be covered by a further layer, which is not shown here in detail.

A discharge zone 66 is formed around the discharge electrode 64 and on the outer side toward the openings 48. Furthermore, due to the voltage differential between the induction electrode 62 and the discharge electrode 64, electric current flow is generated that, in turn, causes heating of the ceramic half 60. Furthermore, this heating of the ceramic half 60 effects convection of the air surrounding the discharge electrode 64. Thus, for example, oxygen-containing air 68 can penetrate through the openings 48, thus, in the present embodiment of the apparatus 12, through the slots 50, into the region of the inner end 42 and into the housing 40, as illustrated by arrows 70. This inflowing $O_2$-containing air 68 is then converted at the discharge electrode 64 at the discharge zone 66. During this conversion, the oxygen molecules are broken up due to the voltage in the discharge zone thereby forming atomic oxygen and triatomic oxygen, thus ozone ($O_3$). Due to the above-described convection, the ozone-containing air 72 formed in this manner is then conveyed back out of the internal chamber 54 of the housing 40. The further mode of action of the ozone-containing air 72 will be explained in more detail later in connection with the FIGS. 8 and 9.

In order to obtain suitable power to the ozone generator 56, cables 56 extend through the upper part of the internal chamber 54 of the housing 40 to the ozone generator 56. These cables 76 preferably end at the outer end 44 at the power connector 36 of the handle 34.

In an alternate embodiment that is not shown in detail, the cover 46 can be replaced by a fan in order to enhance the mentioned convective drawing of air into the internal chamber 54. Thus, the ventilator is arranged at the inner end 42 of the housing 40.

Figure 5:
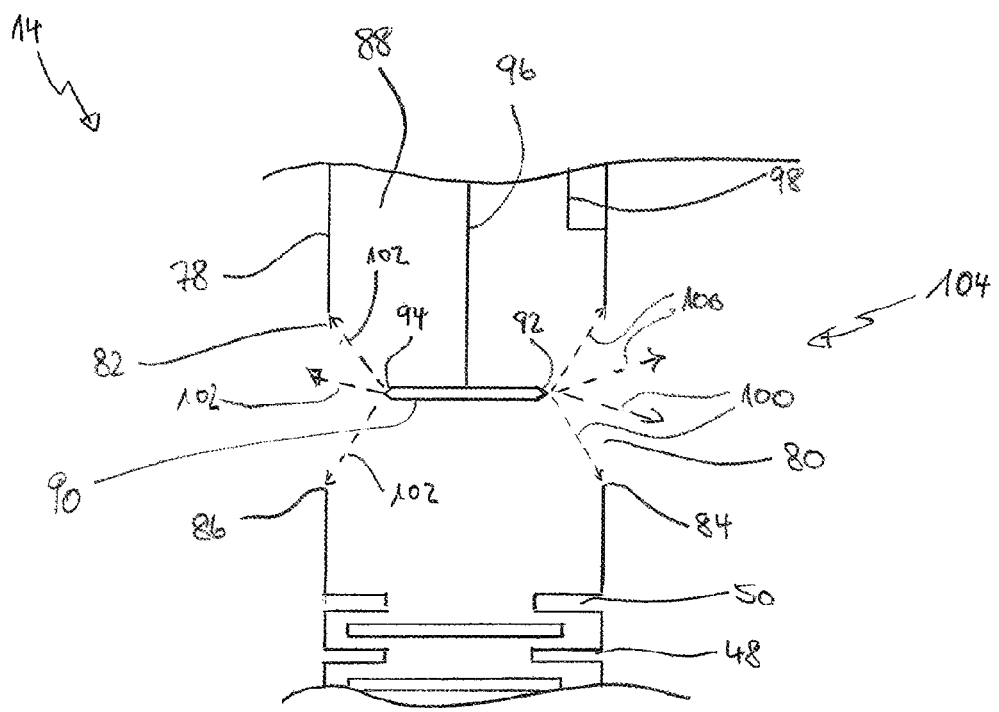
FIG. 5 is a view like FIG. 4 of a third embodiment of the invention.

The apparatus 14 illustrated in FIG. 5 is comparable to the apparatuses 10 and 12 and comprises in particular the openings 48 shown in the apparatus 12 in the form of slots 50 at the inner end 42. These openings 48 are arranged in a housing 78 of the apparatus 14. The remaining regions of the outer end 44, which are not shown in detail here, with the handle 34 and the sealing element 26 are substantially identical to the apparatuses 10 and 12.

With regard to FIG. 5, the housing 78 has openings 80 and 82 located above the openings 48, that is offset axially outward toward the outer end 44. These openings 80 and 82 are illustrated here in section and, apart from that, are of circular shape. As a result, the openings 80 and 82 have circular edges 84 and 86.

The housing 78 of the apparatus 14 also has an internal chamber 88 holding a elongated, diametrally extending, and pointed electrode 90. This pointed electrode is characterized by pointed ends that have tips 92 and 94 roughly centered in the respective circular holes 80 and 82, that is centered within the circular edges 84 and 86 and pointing substantially to the center of the respective openings 80 and 82. The pointed electrode 90 is connected to a power source via a supply line 96. Furthermore, a supply line 98 connects the housing 78 to the power source. Thus, the housing 78 also forms an electrode 99. Two supply lines 96 and 98 extend through the internal chamber 88 of the apparatus 14 and/or of the housing 78 to the outer end 44, where they preferably end at the power connector 36 in the handle 34 and thus can be connected to a power source. Thus, in the present case, there are two electrodes, one of which is formed by the pointed electrode 90, while the other electrode 99 is formed by the housing 78 of the apparatus 14.

If now voltage is applied between the pointed electrode 90 and the housing 78, electrons move from the tips 92 and 94 of the pointed electrode 90 in the direction toward the edges 84 and 86 of the openings 80 and 82. Thus, an electron spray is formed that is illustrated by the dashed arrows 100 and 102. Due to this electron spray, the molecular oxygen in the air is also broken up and, among other things, ozone is formed. Thus, the pointed electrode 90 and the housing 78 as the electrode 99 together form an ozone generator 104. This ozone generator 104 is arranged in the internal chamber 88 of the housing 78.

In the electron spray, the electrons and, if applicable, ions and radicals already formed, are accelerated toward the openings 80 and 82 and/or toward the edges 84 and 86 thereof, whereupon they sometimes also move outside the internal chamber 88 of the apparatus 14. As a result, convection already mentioned above is also enhanced. Oxygen-containing air 68, which is not shown here in detail, can penetrate through the slots 50 into the internal chamber 88, is conveyed to the pointed electrode 90 and there, due to the electron sprays 100, 102, is conveyed through the openings 80 and 82 from the internal chamber 88 and thus from the housing 78 to the outside again. Due to the electrical discharges, ozone and therefore also ozone-containing air 72 is now formed and transported into the interior of a container to be disinfected. Due to the formation of ozone and other reactive species, such as O- or OH-radicals, by the respective electron sprays 100 and 102 instead of the formation directly on an electrode surface, no formation of coats by organic molecules potentially present in the oxygen-containing air 68 takes place on the pointed electrode 90. This arrangement therefore requires very little maintenance. Both the ozone generator 104 and the ozone generator 56 can generate ozone in dry air and in particular in moist air. This, on the one hand, is particularly advantageous for disinfecting containers that contain residual moisture such as, for example wooden barrels, and, on the other, it also opens the possibility for providing hydrogen peroxide at the same time. The latter possibility is explained in more detail hereinafter.

Figure 6:
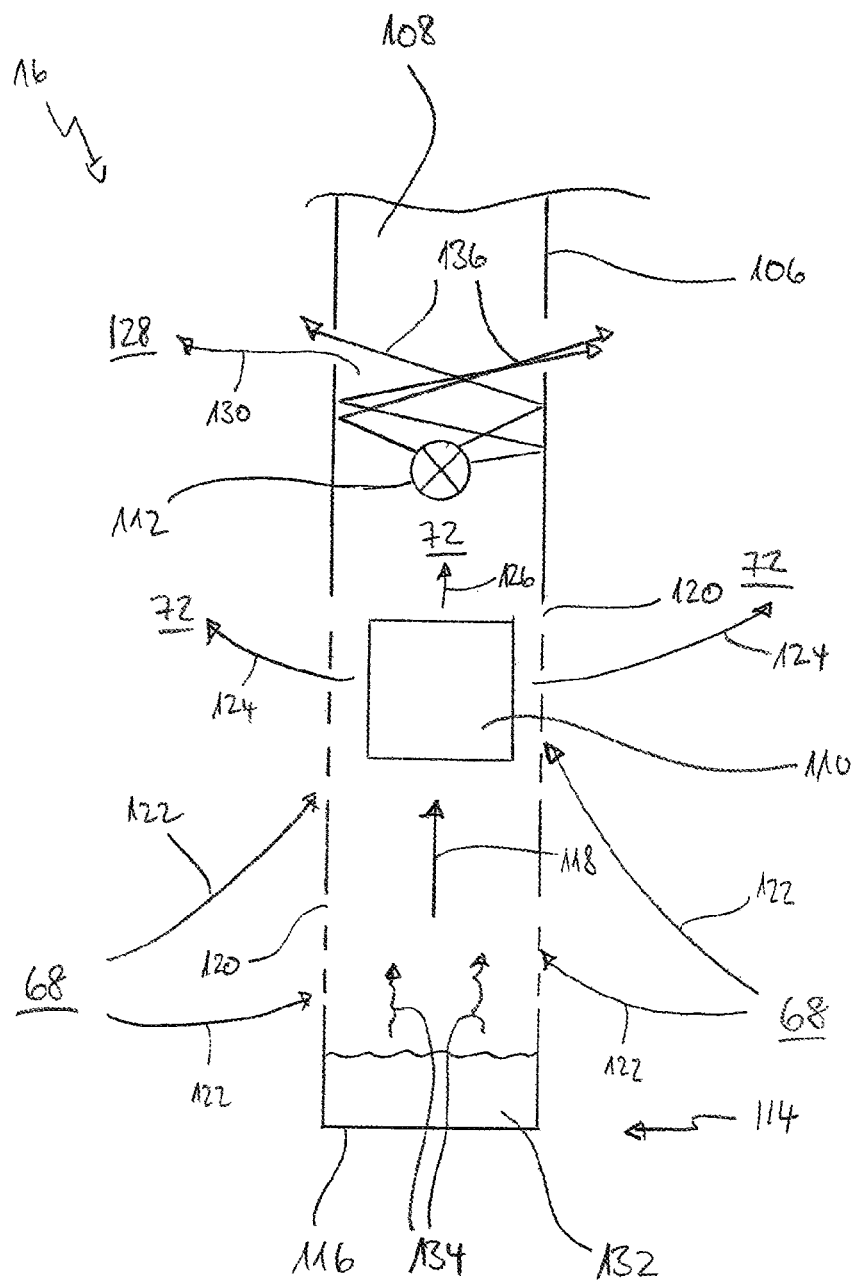
FIG. 6 is a view like FIG. 4 of a fourth embodiment of the invention.

The embodiment of the apparatus 16 shown in FIG. 6 also is comparable to the apparatuses 10 and 12. Here, the part of the outer end that is not shown can be regarded again as substantially identical to the same parts of the apparatuses 10 and 12. Apart from that, the apparatus 16 has a housing 106 with an internal chamber 108. In addition to an ozone generator 110, which is illustrated here only schematically, a UV light source 112 is provided in this internal chamber. The embodiment of the ozone generator 110 can be selected depending on the requirements and is preferably one of the above-described ozone generators 56 or 104. Furthermore, the housing 106 has an inner end 114 that is closed by a cover 116. Both the ozone generator 110 and the UV source 112 generate heat, resulting again in convection of air. Air convection within the housing 106 is indicated here in FIG. 6 by an arrow 118. At the inner end 114, the housing 106 of the apparatus 16 likewise has a plurality of openings 120. These openings are indicated here only schematically in the illustration of FIG. 6. In this connection it is possible to provide in the apparatus 16 both an arrangement of round holes 30 that is comparable to the apparatus 10 and slots 50 corresponding to the apparatus 12.

Due to the convection illustrated schematically at 118 118, oxygen-containing air 68 flows through these openings 120 into the internal chamber 108 of the housing 106 as shown by arrows 122. The oxygen-containing air 68 is then converted at the ozone generator 110 into ozone-containing air 72. The latter, as indicated by the arrows 124, then flows through further openings 120 out of the internal chamber 108 of the housing 106 to the outside again. In addition, further ozone-containing air 72 also flows according to the convection 118 within the internal chamber 108 toward the UV light source 112. This is indicated by a further arrow 126. In presence of air humidity, that is, in presence of water or water vapor, and under the influence of the UV radiation of the UV light source 112, this ozone-containing air 72 in the internal chamber 108 can now form hydrogen peroxide. The resulting hydrogen peroxide-containing air 128 can then also flow outward through the openings 120. This is indicated by a further arrow 130.

Since hydrogen peroxide is likewise very well suited as a disinfectant, according to a preferred embodiment forming hydrogen peroxide is facilitated. For this purpose, water, preferably distilled water 132, is also provided at the outer end 114 in the internal chamber 108 of the housing 106. Through the above-described convection 118 and the inflow of oxygen-containing air 68 according to the arrows 122, water vapor formed over the distilled water moves toward the ozone generator 110 and the UV light source 112. This is also indicated by arrows 134. Facilitating the formation of water vapor from the distilled water 132 can also be carried out through heat generation of the ozone generator 110 and the UV light source 12. Furthermore, a separate heat source or another vapor-generating element can be provided so as to specifically evaporate the distilled water 132.

In addition to the formation of hydrogen peroxide within the internal chamber 108 of the housing 106, this formation also takes place outside of the housing 106. For this purpose, UV light beams 136 are emitted through the openings 120 to the outside, as indicated by the arrows 136. In the embodiment of the apparatus 16 shown here, no openings 120 are provided at the level of the UV light source 112 so that the UV light beams 136 are first reflected on the inner wall of the housing 106, and therefore enhancement of the UV light beams 136 takes place. After exiting the housing 106, these UV light beams 136 can also ensure that ozone present outside of the housing 106 reacts with water so as to form hydrogen peroxide. Furthermore, the UV light radiation in the form of the light beams 136 facilitates the formation of chain reactions that can be induced and maintained by UV light, and therefore also facilitates the degradation of organic compounds present within a container to be disinfected. Thus, this makes a further contribution to disinfection and removal of undesirable and harmful odors and flavoring substances.

Figure 7:
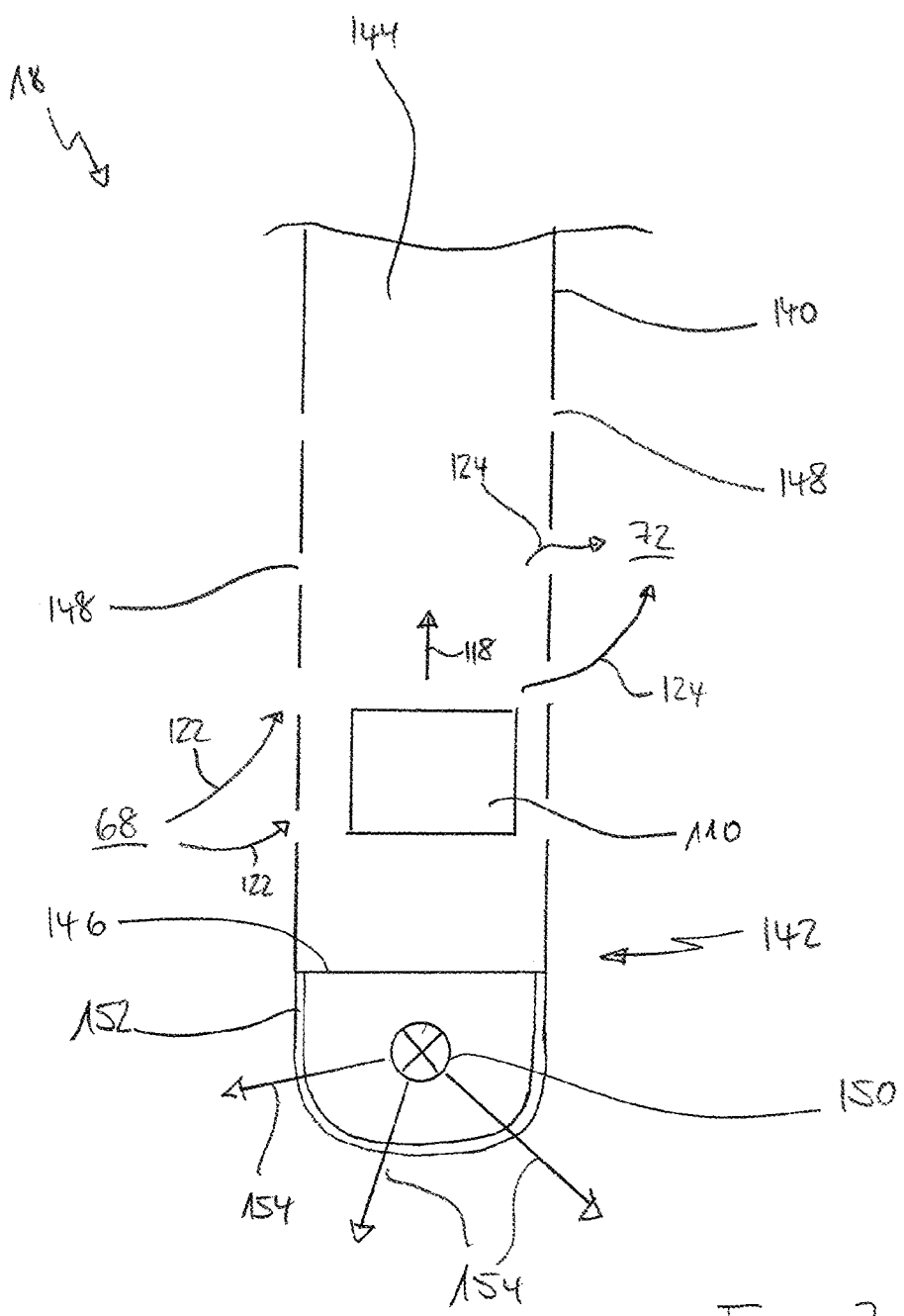
FIG. 7 is a view like FIG. 4 of a fifth embodiment of the invention.

The embodiment of the apparatus 18 in FIG. 7 is comparable to the apparatuses 10 and 12 of the present invention. This means that in particular the outer end with the handle and the sealing element, which region is not shown here, is configured to be identical to these apparatuses.

The apparatus 18 further comprises a housing 140 that has an outer end 142 and an internal chamber 144. The internal chamber 144 is closed at the outer end 142 by a cover 146. The housing 140 further has openings 148 that, as in the apparatus 16, can be configured as round holes 30 or slots 52, comparable to the embodiments of the apparatuses 10 and 12. Furthermore, at the outer end 142, an ozone generator 110 is provided that, as in the apparatus 16, can be configured according to one of the above-embodiments for ozone generators 56 or 104 of the apparatuses 12 and 14. Due to the heat development during the ozone generation in the ozone generator 110, a convection 118 is created again, as already explained in connection with the apparatus 16. As a result, oxygen-containing air 68 flows into the openings 148 of the housing 140 according to the arrows 122. Then, ozone-containing air 72 is generated at the ozone generator 110 in the internal chamber 144 and, due to the convection, is conveyed according to the arrows 124 through the openings 148 and from the housing 140 to the outside again.

In addition, the apparatus 18 has a UV light source 150 at the outer end 142. In this embodiment, this UV light source is surrounded by a UV-light-permeable protective cap 152. This UV light source 150 emits UV light in the form of beams 154 radiating outward into the interior of a container to be disinfected. Due to the humidity in the air and generally in the interior of the container to be disinfected, the supply of ozone-containing air 72 can now result again in formation of hydrogen peroxide under the influence of the UV light beams 154. Furthermore, there is also the possibility here that chain reactions can be started and/or maintained by the UV light beams in the interior of the respective container. Thus, here too, thorough disinfection and cleaning takes place with regard to undesirable organic compounds such as, for example odorous or flavoring substances. Unlike the embodiment of the apparatus 16 where hydrogen peroxide and similar compounds are generated exclusively in the interior of the container. In contrast to this, hydrogen peroxide is also generated in the internal chamber 144 in the apparatus 16 and is fed in this manner as hydrogen peroxide-containing air 128 to the ambient air in the interior of the respective container.

In addition to generating hydrogen peroxide, the UV light sources 112 and 150 of the apparatuses 16 and 18 can also be used, after the respective ozone generator 110 is switched off, to provide for accelerated decomposition, that is, for faster degradation of the remaining ozone in the interior of the container. This can also be applied to the apparatuses 10, 12 and 14 if they are modified with UV light sources.

In connection with the FIGS. 8 and 9 and the above explanations, the functional principle and accordingly also the method according to the invention will now be explained in more detail.

Figure 8:
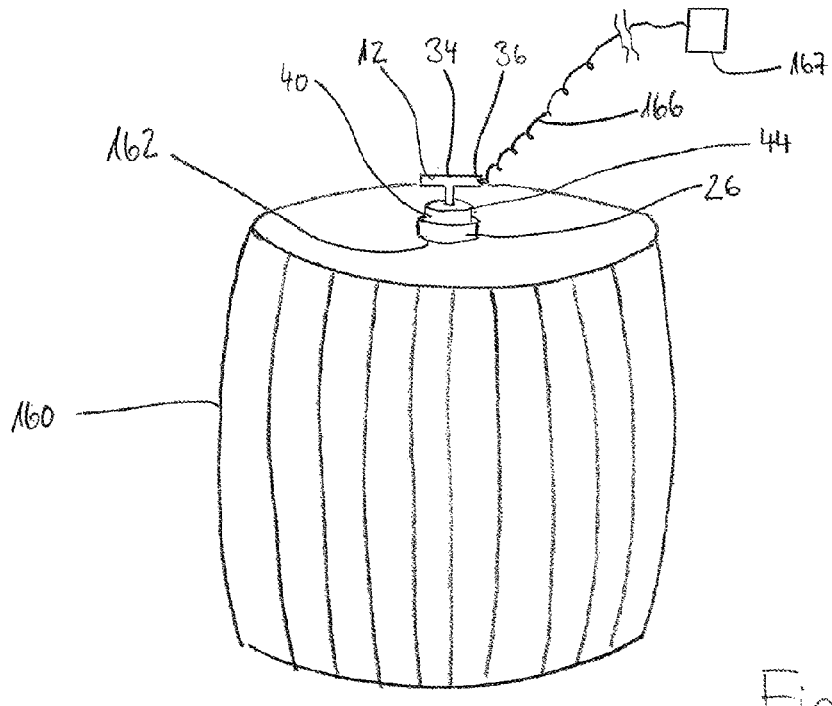
FIG. 8 is a small-scale perspective view of a wooden barrel an apparatus according to the invention corresponding to FIG. 2.

For this purpose, FIG. 8 shows a wooden container in the form of a wooden barrel 160. This wooden barrel 160 has an opening 162 at its upper end, thus in the cover. This opening 162 is usually round. The apparatus 12 according to the invention is inserted into this wooden barrel 160 through the opening 162.

In addition to the exemplary configurations of the wooden barrel 160 shown here, other configurations of wooden barrels, in which the respective opening is provided, for example in a barrel stave, are also possible. There can also be two or more openings, and the openings that do not receive an apparatus according to the invention are then optionally closed, as will be explained below. Furthermore, it is also possible that both in the cover and in the barrel stave, the position of the respective opening varies so that the opening does not necessarily have to be arranged centrally, as shown here for illustration purposes. The following illustrations in connection with the wooden barrel 160 can be applied to the above-described barrels and other barrels having alternate constructions. The functional principle of the apparatus according to the invention and of the method according to the invention are therefore not bound to the illustrated shape and configuration of the wooden barrel 160.

Although herein and hereinafter the illustrations of the functional principle of the apparatuses according to the invention and the method according to the invention are based on the apparatus 12, it is clear that the corresponding explanations can also be applied to the apparatuses 10, 14, 16 and 18 in an analogous manner.

Figure 9:
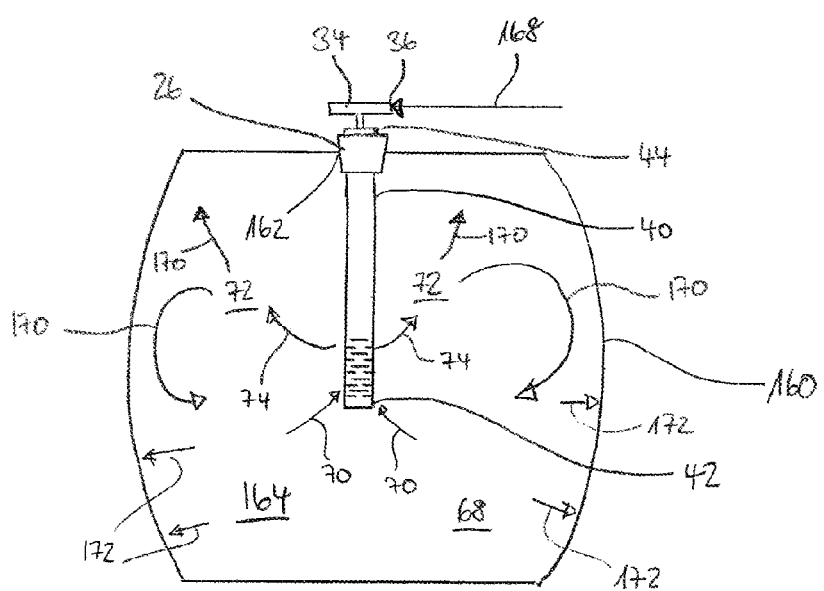
FIG. 9 is a schematic vertical section through the barrel of FIG. 8.

From the illustration of the FIGS. 8 and 9 it is apparent that the opening 162 receives the apparatus 12 via the sealing element 26. In this way, the outer end 44 with the handle 34 and the connector 36 is positioned outside the container, thus, of the wooden barrel 160. In contrast to this, the remaining part including the inner end 42 and the openings 48 and the ozone generator 56 in the internal chamber 54 of the housing 40 are positioned in the interior 164 of the wooden barrel 160. Since the wooden barrel 160 has no other openings, or they are preferably closed, the interior 164 and therefore also the wooden barrel 160 are sealed.

Provided that no or no noticeable specific gas exchange has taken place, oxygen-containing air 68 can be found in the interior 164 of the barrel 160.

A cable 16 from the power connector 36 is connected to a power source 167 so as to be able to feed current through the cable 76 to the ozone generator 56. Furthermore, the power supply is indicated by an arrow 168 in FIG. 9.

Once the power supply 168 is activated, a corresponding discharge and a corresponding current flow takes place at the ozone generator 56 so that the dielectric ceramic half 60 heats up. As in all other embodiments of ozone generators 104 and 110, this results in the mentioned and already explained convection. Ozone is discharged by the ozone generator 56 inside the wooden barrel 160, that is, in the interior 164. This takes place according to the invention by generating the ozone in the interior 164.

Due to the mentioned convection, oxygen-containing air 68 flows, as indicated by arrows 70, into the internal chamber 54 of the housing 40. In the course of this, this oxygen-containing air 68 flows through the openings 48 into the internal chamber 54 and is guided into the discharge zone 66, as already explained, for example in connection with FIG. 4. There, the desired ozone generation is carried out by the ozone generator 56. The ozone-containing air 72 formed in this manner is then directed again, as indicated by arrows 74, through the openings 48 out of the internal chamber 54 and into the interior 164 of the barrel 160. Due to the convection and/or by diffusion, distribution of this ozone-containing air 72 in the interior 164 is achieved. This is indicated by arrows 170. As a result, the ozone-containing air 72 and therefore the ozone can be distributed in the entire interior 164 and thus reaches the entire inner surface of the wooden barrel 160. Thus the ozone can even penetrate from the interior 164 into the wood of the barrel 160. This effect of the ozone on the inner walls of the wooden barrel 160 is likewise indicated by arrows 172. The result is a disinfection of the entire interior 164 of the wooden barrel 160, both with regard to aerobic and anaerobic microorganisms. Furthermore, undesirable odorous or flavoring substances are eliminated.

Using these apparatuses 10, 12, 14, 16 and 18 according to the invention takes place by gripping the apparatus in each case, for example at the handle 34 and inserting it into an opening 162 of the wooden container, here, of the wooden barrel 160. This action seals the wooden container by the sealing element 26. The power supply, indicated by the arrow 168, causes ozone to be generated by the ozone generator, for example the ozone generator 56 or 104. By continuously supplying power, the generation of ozone is therefore also carried out continuously. Accordingly, air movement illustrated by the arrows 70, 74, 170 and 172 and therefore also the disinfection effect are likewise to be regarded as continuous. When the disinfection or reaction of the ozone is completed and the ozone reacts again so as to form $O_2$, oxygen-containing air 68 thus is present again, which can enter into a next cycle that begins with the arrow 70. If this conversion back into $O_2$ is to be accelerated after completed disinfection, irradiation of the interior of the wooden container with UV light after switching off the ozone generator can be provided.

As has been explained in particular in connection with FIGS. 6 and 7, that is, with the apparatuses 16 and 18, UV light sources 112 and 150 can be also provided. Besides the above-described ozone removal, it is possible in this manner to facilitate the generation of hydrogen peroxide, which likewise can result in a disinfection of the surface and generally in the interior 164 of a wooden barrel 160. In order to further facilitate this, it is possible according to FIG. 6 and the explanations in connection with the apparatus 16 to also provide (distilled) water so that the corresponding water vapor 134 can already be available during the ozone generation. The effects of the hydrogen-containing air 128 obtained in this manner are then comparable with and analogous to the explanations in connection with FIG. 9 and the ozone-containing air 72.

Both hydrogen peroxide-containing air 128 and ozone-containing air 72 react over time residue-free and therefore, after switching off the ozone generation, no longer pose a health risk.

I claim:

1. A method of disinfecting an interior of a container having an opening but otherwise closed, the method comprising the steps of:
    fitting into the container through the opening an elongated housing having an outer end carrying a seal and an inner end and a wall extending between the ends, formed with a plurality of throughgoing holes, and forming a reaction chamber;
    fitting the outer end with the seal in the opening to close the container to substantially prevent fluid flow into and out of the interior;
    providing an ozone generator inside the housing; and
    generating ozone in the chamber inside the closed container solely from air inside the container with the ozone-generator such that the generated ozone passes out through the holes into the container and internally disinfects the container without escaping from the container and without any fluid being drawn into the container during ozone generation.

2. The disinfecting method defined in claim 1, wherein the housing is cylindrically tubular.

3. The disinfecting method defined in claim 2, wherein the housing is of metal.

4. The disinfecting method defined in claim 1, wherein the holes in the wall are generally circular.

5. The disinfecting method defined in claim 1, wherein the holes in the wall are slots.

6. The disinfecting method defined in claim 1, further comprising:
    a connector on the outer end outside the container for electrically powering the ozone generator.

7. The disinfecting method defined in claim 1, wherein the ozone generator has inside the chamber:
    an induction electrode,
    a discharge electrode, and
    a dielectric body between the electrodes.

8. The disinfecting method defined in claim 1, wherein the ozone generator includes an inner electrode inside the chamber and having a point spaced from a periphery of the housing, the housing being conductive and forming a counterelectrode to the inner electrode.

9. The disinfecting method defined in claim 1, further comprising:
    an ultraviolet-light source in or on the housing offset from the outer end.

10. The disinfecting method defined in claim 1, wherein the housing at least at the inner end is formed of stainless steel, plastic, aluminum, silver, or palladium.

11. The disinfecting method defined in claim 1, wherein the housing is formed at least partly on a surface of its inner end of aluminum oxide, manganese oxide, or copper oxide.

12. The disinfecting method defined in claim 1, wherein the generation of ozone is continuous for a predetermined time.

13. The disinfecting method defined in claim 1, further comprising:
    providing an ultraviolet-light source in the closed container; and
    generating ultraviolet light in the interior while generating ozone.

14. The disinfecting method defined in claim 13, further comprising the step of:
    creating steam in the interior while generating ultraviolet light to create hydrogen peroxide.

15. The disinfecting method defined in claim 1, further comprising the step of:
    heating the drawn-in air while generating ozone to create in the container a convective gas flow through the housing.

* * * * *